United States Patent
Roth

(10) Patent No.: US 7,710,561 B2
(45) Date of Patent: May 4, 2010

(54) TRANSSPECTRAL ILLUMINATION

(76) Inventor: Richard Stefan Roth, 1947 Oak Ave., Boulder, CO (US) 80304

( * ) Notice: Subject to any disclaimer, the term of this patent is extended or adjusted under 35 U.S.C. 154(b) by 0 days.

(21) Appl. No.: 12/126,078

(22) Filed: May 23, 2008

(65) Prior Publication Data

US 2009/0290149 A1 Nov. 26, 2009

(51) Int. Cl.
*G01J 3/40* (2006.01)
(52) U.S. Cl. .................................................. 356/302
(58) Field of Classification Search ................. 356/300, 356/302
See application file for complete search history.

(56) References Cited

U.S. PATENT DOCUMENTS

| | | | | |
|---|---|---|---|---|
| 5,808,738 | A | * | 9/1998 | Garcia-Rubio ............... 356/309 |
| 2007/0012877 | A1 | * | 1/2007 | DiMarzio et al. .......... 250/341.3 |
| 2008/0156991 | A1 | * | 7/2008 | Hu et al. .................... 250/341.1 |

OTHER PUBLICATIONS

International Search Report and Written Opinion via US International Searching Authority for PCT/US09/44814, dated Nov. 24, 2009, 12 pages.
International Search Report mailed Nov. 24, 2009; International Application No. PCT/US2009/044814, 9 pages.

* cited by examiner

*Primary Examiner*—Tarifur Chowdhury
*Assistant Examiner*—Abdullahi Nur
(74) *Attorney, Agent, or Firm*—Townsend and Townsend and Crew LLP

(57) ABSTRACT

Methods are disclosed of generating a visible image of an object or scene under study. At least a portion of the object or scene under study is illuminated with light outside a visible portion of an electromagnetic spectrum. Light scattered by the object or scene under study is received. The received light is spectroscopically analyzed for volume elements of the object or scene under study. A respective qualitative feature of the object or scene under study is identified at least one of the volume elements. Visible light is propagated to the at least one of the volume elements according to the respective qualitative feature of the object or scene under study at the at least one of the volume elements.

28 Claims, 5 Drawing Sheets

TRANSSPECTRAL ILLUMINATION

BACKGROUND OF THE INVENTION

This application relates generally to imaging. More specifically, this application relates to imaging objects or scenes electromagnetically using radiation with frequencies outside the visual spectrum.

Many methods of acquiring information about objects and/or scenes rely on the same fundamental process: the object or scene is irradiated and the response of the object or scene to the radiation is detected. This may be performed using a variety of different types of radiation, including the very familiar electromagnetic and acoustic radiation, as well as less common forms of radiation such as electron-beam, neutron beam, proton-beam, pion-beam, and other types of radiation. In addition to the ability to use these different types of radiation to extract information about objects, it is possible to detect different response when the energy of the radiation is changed.

Electromagnetic and acoustic radiation are especially familiar because they are the two forms of radiation that are most relied on by human beings in acquiring information about objects in the form of vision and hearing. The human sense of vision represents nothing more than the use of the human eye and related neurological structure as an electromagnetic detector that is sensitive to certain wavelengths of light. When an object is illuminated by light, it reflects the light in ways that the human eye can detect to provide information that the human brain may use to ascertain the type of material of the object, its shape, its texture, and so on. Human hearing functions in the same way, with the ear and related neurological structure acting as an acoustic detector sensitive to certain wavelengths of sound. When an object is irradiated by sound, the object reflects the sound in ways that the human ear can used to provide information usable by the human brain for similar kinds of analyses.

One limitation to both human vision and hearing is that the detection range provided by the human eye and ear are relatively narrow. Many objects respond to electromagnetic and/or acoustic radiation at wavelengths that are outside the ability of human senses to detect. For example, it is well known that only certain human tissue is transparent at x-ray wavelengths while other tissue is opaque, causing x-ray illumination to be a very widely used diagnostic tool. Similarly, the use of ultrasonic acoustic waves permits diagnostic information to be acquired that is not directly possible using human senses.

But while it is possible to cause objects to generate a response using radiation outside the detection range of human senses, that response must often still ultimately be evaluated by human beings who remain limited by their biological sensory range. This is true, for instance, in cases where the information is used in medical diagnostics and treatment. For example, the use of x-rays and ultrasound can provide information to a physician about the presence of a malignancy, but only when the information is converted into a form that can be understood by the physician. This is most commonly done by rendering an image in the visual spectrum that corresponds to the object and presenting this image on a planar surface, such as on a screen or a piece of paper. The image is then viewed independently of the original object and inferences are made about the original object.

This general approach has had much success in providing such things as x-ray images that may be viewed by physicians before they begin surgeries, and the like. But the approach is inherently limited by divorcing the generated image from the object being imaged in space and in time. There is accordingly a need in the art for improved methods of imaging objects using radiation outside the range of direct human detection.

BRIEF SUMMARY OF THE INVENTION

Embodiments of the invention provide methods of generating a visible image of an object or scene or scene under study. At least a portion of the object or scene under study is illuminated with light outside a visible portion of an electromagnetic spectrum. Light scattered by the object or scene under study is received. The received light is spectroscopically analyzed for a plurality of volume elements of the object or scene under study. A respective qualitative feature of the object or scene under study is identified at least one of the plurality of volume elements. Visible light is propagated to the at least one of the plurality of volume elements according to the respective qualitative feature of the object or scene under study at the at least one of the plurality of volume elements.

In some cases, the at least one of the plurality of volume elements is each of the plurality of volume elements. In different embodiments, the light outside the visible portion of the electromagnetic spectrum may comprise a frequency between 0.1 and 100 THz, may comprise a frequency between 0.1 and 30 THz, or may comprise a frequency between 1 and 10 THz. The light scattered by the object or scene under study may comprise reflected light and/or may comprise transmitted light in different embodiments.

In some instances, polarization states of the light may be exploited. For example, when the at least a portion of the object or scene under study is illuminated, the light outside the visible portion of the electromagnetic spectrum may be polarized with a first polarization; this may be accompanied polarizing the light scattered by the object or scene under with a second polarization. The first and second polarizations are in a substantially crossed configuration.

In addition, certain embodiments of the invention may share part of the optical path for the nonvisible and the visible light. Specifically, in such cases, illuminating the at least a portion of the object or scene under study comprises propagating the light outside the visible portion of the electromagnetic spectrum along an optical path to the object or scene under study. Propagating the visible light to each of the plurality of volume elements then comprises propagating the visible light along at least a portion of the optical path.

A number of different optical conditions may be used in different applications of the invention. For example, it some cases, the light outside the visible portion of the electromagnetic spectrum is generated by filtering the light. Other conditions under which the object or scene under study may be illuminated include with the use of a substantially continuous beam of light or with a modulated or pulsed beam of light.

The embodiments of the invention may find a variety of applications. For example, in one embodiment, the object or scene under study comprises biological tissue. In another embodiment, propagating visible light to the at least one of the plurality of volume elements comprises propagating a wavelength of light outside the human visible spectrum to the at least one of the plurality of volume elements; a reflection is received from the at least one of the plurality of volume elements with equipment configured to provide a visible image at the wavelength of light.

Methods of the invention may also be embodied in systems for generating a visible image of an object or scene under study. The system comprises a light source, a light detector, and a controller. The controller is in communication with the light source and light detector and has instructions to implement the methods as described above.

BRIEF DESCRIPTION OF THE DRAWINGS

A further understanding of the nature and advantages of the present invention may be realized by reference to the remaining portions of the specification and the drawings wherein like reference labels are used throughout the several drawings to refer to similar components. In some instances, reference labels include a numerical portion followed by a latin-letter suffix; reference to only the numerical portion of reference labels is intended to refer collectively to all reference labels that have that numerical portion but different latin-letter suffices.

DETAILED DESCRIPTION OF THE INVENTION

Embodiments of the invention permit direct visualization of features of an object using light at frequencies that are not visible to the human eye. In particular embodiments, these frequencies may encompass terahertz frequencies, which include frequencies between 0.1 THz and 100 THz. In various specific embodiments, the frequencies used are within a narrower range, such as between 0.1 THz and 30 THz or between 1 THz and 10 THz.

Briefly, embodiments of the invention operate by forming an image on an object or scene under study on a detector array suitable for detecting light of the nonvisible frequencies used. The "object under study" may comprise a static object, a dynamic object, or a scene in various of the embodiments. The image may be spectroscopically analyzed over a plurality of voxels, with a "voxel" referring to a pixelated region in three-dimensional space analogous to a "pixel" used in defining two-dimensional regions. Such an analysis yields at least qualitative information about each voxel that may in some embodiments represent identification of the composition of material at the imaged point of the object under study. Light in the visible spectrum may be generated and projected onto the object under study to provide a representation of the image that is visible to the human eye. In some instances, the wavelength or intensity of the visible light may be selected to correspond to the identified composition of the object at the corresponding voxel. The projection onto the object thus provides a visible representation of the object that allows discrimination of different properties of the object derived from nonvisible illumination. In addition, in some applications, the generated and projected light may be slightly outside the range of human vision, but within the frequency range of vision-aiding systems or equipment, such as sight vision equipment. The visible representation is thus obtained with the aid of the vision-aiding equipment.

Figure 1:
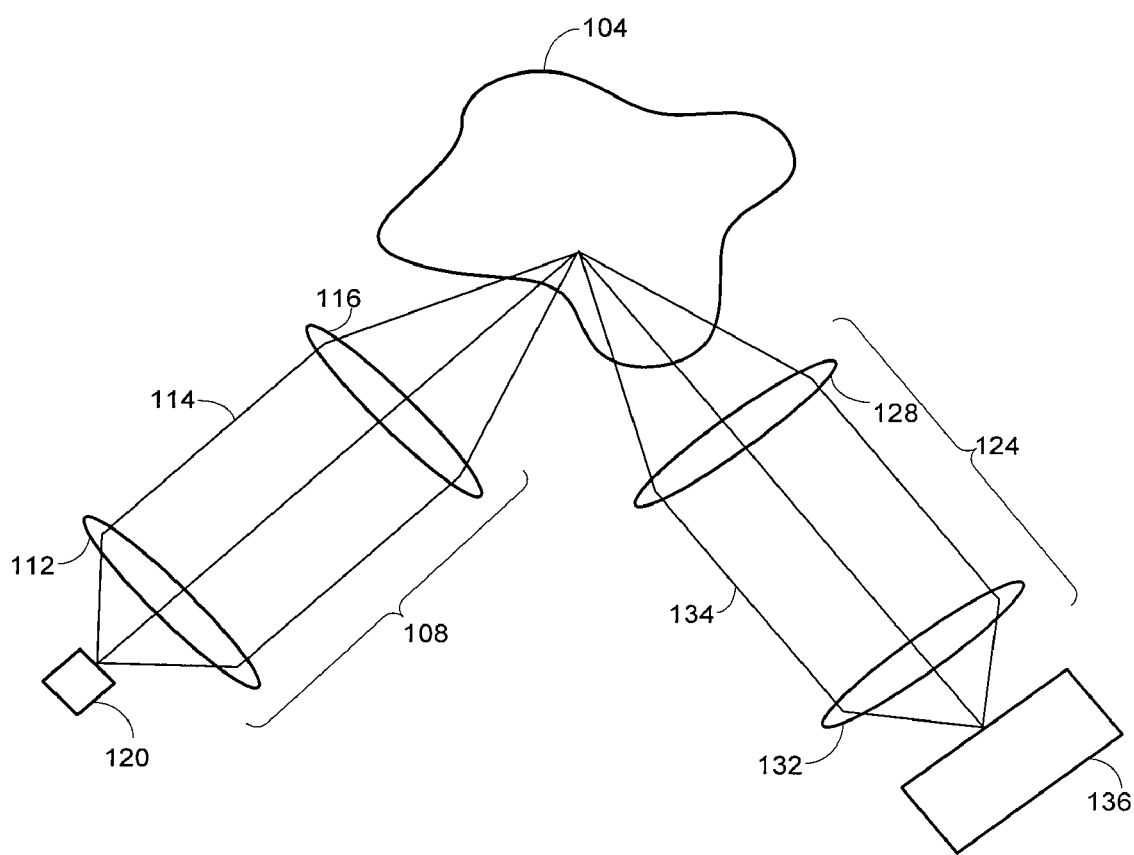
FIG. 1 provides a schematic view illustrating general features of an illuminator in accordance with embodiments of the invention.

A basic overview of how systems of the invention may be configured is provided with the schematic illustration of FIG. 1, in which the object under study is designated with reference number 104. In this drawing, illumination optics are generally illustrated on the left part of the figure with detection optics illustrated on the right part of the figure. The illumination optics include a light source 120, which may comprise both a visible-light source and a nonvisible-light source. In embodiments that use terahertz illumination, the nonvisible-light source may comprise a source of electromagnetic radiation at frequencies between 0.1 THz and 100 THz, between 0.1 THz and 30 THz, or between 1 THz and 10 THz in different embodiments. Suitable terahertz sources may include broadband pulse lasers over frequency range of about 0.2 to 5.0 THz; examples of suitable sources include those made of GaP and ZnTe nonlinear crystals, among other types of materials. Each of the visible- and nonvisible-light sources may provided light that is broadband across the respective relevant portions of the electromagnetic spectrum or light comprises a plurality of subportions of the respective relevant portions. Each of those subportions may in turn be provided as spectral bands or as one or more discrete, substantially monochromatic beams. In the particular case of the nonvisible light, the specific spectral structure of the light beam may be designed to comprise light frequencies known to have interactions with expected compositions of the object under study 104. Such an approach also permits delivering higher optical power within a chosen frequency in order to sufficiently excite weak interactions or to enable deeper penetration into the object under study 104. In the particular case of the visible light, the specific spectral structure may be designed to highlight distinctions in the material of the object under study 104 when it is used to project an image onto the object 104.

Illumination of the object under study 104 from light 114 generated by the light source 120 is achieved by an optical train 108 that may include a variety of optical elements used to shape and direct the light to the object under study 104. To simplify the illustration, the optical train is shown as comprising a collimating lens 112 and a focusing lens 116, but it should be appreciated that additional and/or substitute elements may be used, particularly in embodiments where specialized beam shapes are to be used. For example, the illustration of FIG. 1 might comprise spherical lenses or cylindrical lenses in different embodiments, and alternative embodiments might make use of parabolic reflective optics arranged in a configuration to direct a shaped beam to the object under study 104. It will also be evident to those of skill in the art that the beam need not propagate in a single direction as illustrated, but may be optically redirected in some embodiments. Furthermore, while the optical train 108 is shown directing the light 114 to a single point in the object under study 104, the optical train 108 may more generally be configured to illuminate a greater portion of the object 104, either by providing less focused illumination over the object 104 and/or by scanning the light 114 over and/or through the object 104. Examples of illumination structures that may be used thus comprising flying spots, line scans, and staring arrays, among others.

In different embodiments, the light 114 may be provided by the light source 120 as temporally continuous light or as pulsed light. For example, a pulse rate may be sufficiently short that the Fourier spectrum of the light has a bandwidth on the order of hundreds of GHz, combining a useful blend of low resolution with penetration adequate for many applications. Examples of different sources that may be used in different embodiments of the invention include solid-state sources such as Gunn and Impatt oscillators at low frequencies and diode-multiplied Gunn and Impatt oscillators at higher frequency. At relatively high frequencies, a high-power source could be a waveguide-coupled Schottky varactor suitable for continuous-wave operation Detection of light scattered from the object under study 104 may be performed with a similar configuration as illumination. In particular, light reflected from and/or transmitted through the object 104 may be directed using an optical train 124 to a light detector 136. Again, the optical train 124 is shown in simplified fashion as comprising a collimating lens 128 and a focusing lens 132 that in combination direct the scattered light 134 to the detector 136. But the optical train 124 may comprise additional and/or alternative optical elements configured to direct the light 134 and/or to shape the beam as appropriate. For example, the detection optical train 124 might comprise spherical or cylindrical lenses in different embodiment, and alternative embodiments might make use of parabolic reflective optics in lieu of using refractive optics.

Examples of detectors that may be used in different embodiments include photodiode arrays or charge-coupled-device arrays in different embodiments. Detectors may comprise array-pitch devices, microantenna beam-pattern devices, heterodyne array receivers, quantum cascade laser local oscillators, acousto-optic spectrum analyzer arrays, or other structures in various embodiments. In some instances, the detection optical 124 may also comprise a scanning mechanism that is configured to relay light from different portions of the object under study 104 onto the detector 136 in a sequence. The detector may also be configured to be limited in sensitivity to a particular range of the electromagnetic spectrum so that only features that are responsive to that range may be studied.

It is also noted that the drawing of FIG. 1 is intended to be schematic and simplifies certain aspects of physical embodiments of the invention. For example, the drawing shows the illumination optics sharing a common optical path for both visible and nonvisible light, while in some physical embodiments, only a portion of the optical path might be shared or none of the optical path might be shared. The different optical paths that are used may be configured through appropriate use of different optical elements to direct the light as desired.

Figure 2:
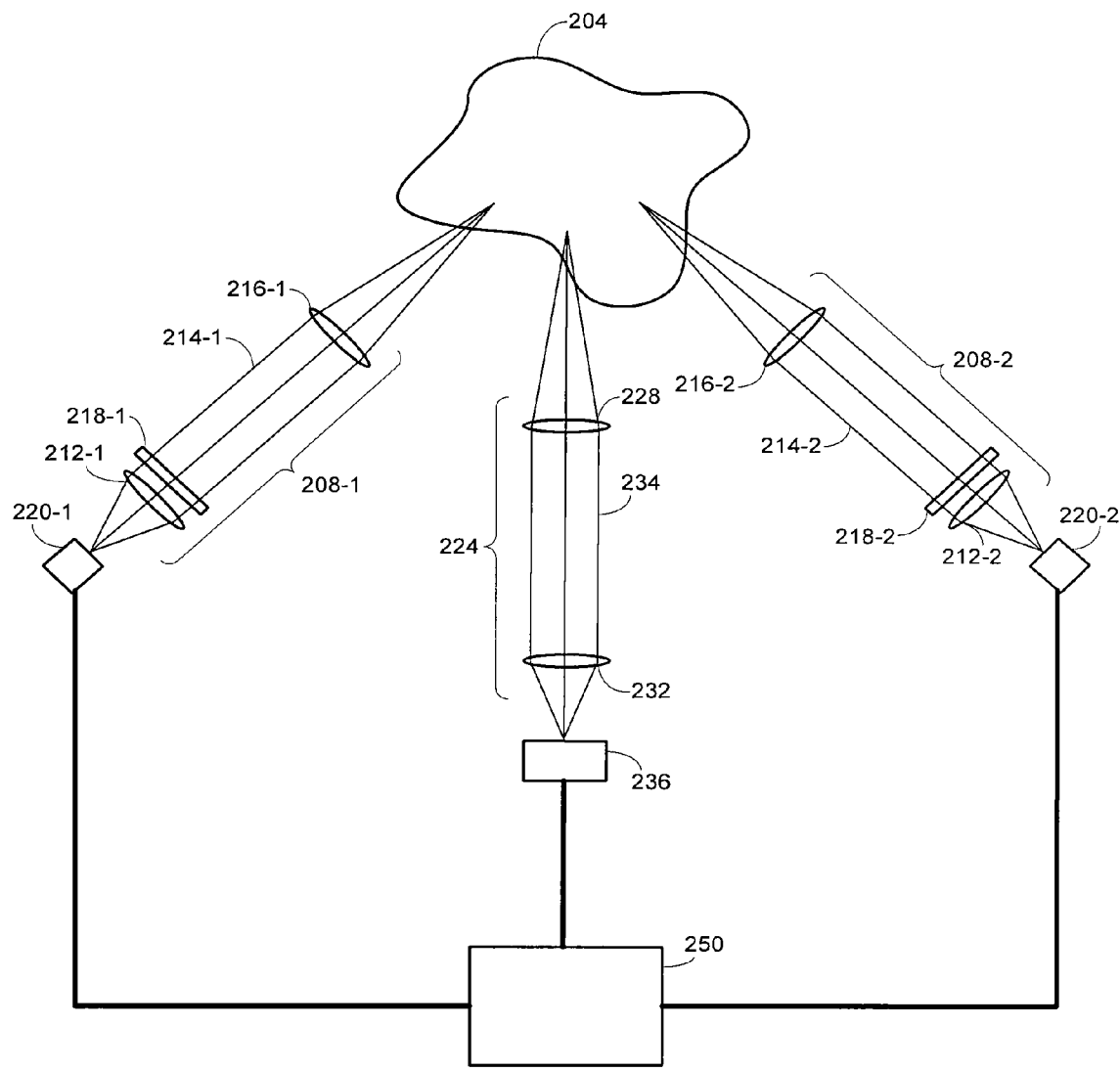
FIG. 2 provides a schematic view of a first structure for an illuminator in accordance with an embodiment of the invention that uses reflected illumination.

A more detailed illustration of a physical structure that may be used is provided schematically in FIG. 2. In this embodiment, two illumination paths are provided and a single detection path is provided. More generally, there may be a plurality of illumination paths and/or a plurality of detection paths in various embodiments. The basic structure of each of the illumination paths is similar to that of the illumination path described in connection with FIG. 1. In particular, each illumination path comprises illumination optics 208 in the form of a collimating lens 212, a focusing lens 216, and a filter 212. In such embodiments, the filter 218 acts to narrow the spectral width of the illumination light 214 and may comprise a single bandpass filter or may comprise a plurality of discrete bandpass filters. In certain specialized embodiments, the filter 218 comprises a continuously variable filter that may move in a combination of linear or rotational motions to change the wavelength of the illumination light. In still other embodiments, the filter 218 comprises a tunable filter, which may be provided as a liquid-crystal tunable filter, an acousto-optical tunable filter, a tunable Fabry-Perot filter or other filter mechanism. The illumination light 214 for each illumination path is provided by a light source 220, which may be provided using any of the structures discussed in connection with FIG. 1.

Light from the light sources 220 is thus directed to the object under study 204, with light scattered from the object 204 being propagated to a detector 236 along a detection path through detection optics 224. The detection optics 224 are shown to have a similar structure to the illumination optics 208, comprising a collimating lens 228 and a focusing lens 232 in the illustrated embodiment. But more generally, they may comprise any optical structure suitable for directing scattering light 234 to the detector 236.

Each of the light sources 220 and detector 236 is controlled by a controller 250 that performs a variety of functions in implementing methods of the invention. The controller 250 may also control the configuration of each of the illumination and detection optical trains to the extent they are configurable in implementing such methods. In particular, the controller 250 may control the timing, during, and wavelength(s) of the illumination light by controlling operation of the light sources 220. It may also control the receipt of light by the detector 236 and perform various analyses as described below in characterizing aspects of the object under study 204. In controlling the light sources 220, it accordingly causes the nonvisible light to be generated as well as the visible light after analysis of information derived from the scattered light. Such visible light may be directed to different portions of the object under study to illuminate it at particular optical characteristics according to wavelength, intensity, time, pulsing, and other characteristics used in discriminating features of the object 204.

Figure 3:
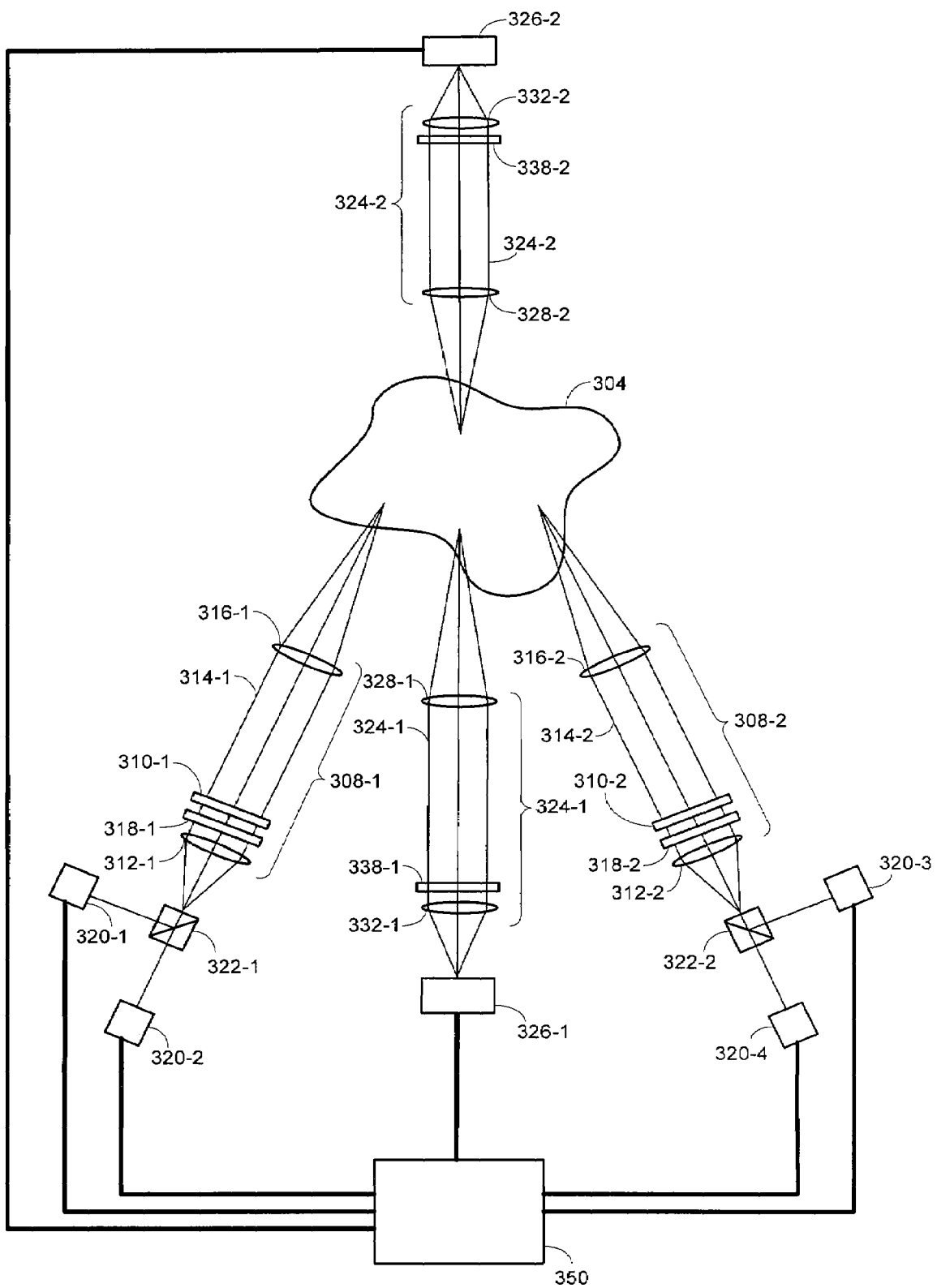
FIG. 3 provides a schematic view of a second structure for an illuminator in accordance with an embodiment of the invention that uses reflected and transmitted illumination.

FIG. 3 illustrates another physical structure that has yet more functionality that the arrangement of FIG. 2. Features that this arrangement comprises include a plurality of detection optics arranged so that both reflected and transmitted light may be collected, polarization elements, and specific optical structures to achieve illumination by both visible and nonvisible light. The use of scattered light that is transmitted through the object under study 304 may provide information different from that achieved solely through the use of reflected radiation. And the use of polarization elements may be used to acquire information about the object 304 at different depths.

In this illustration, a plurality of illumination paths are provided with illumination optics 308, shown in the drawing to include a collimating lens 312, a focusing lens 316, a filter 318, and a polarizer 310. The functions of each of the lenses and the filter are substantially the same as described for similar elements in connection with FIG. 2, and a variety of alternative optical configurations may similarly be used in other embodiments. In the embodiment of FIG. 3, the use of separate light sources 320 for providing the nonvisible and visible light is shown explicitly. For instance, sources 320-1 and 320-3 may provide nonvisible light sources 320-2 and 320-4 may provide visible light, with an optical combiner 322 being interposed before part of the respective optical trains so that the optical pathways followed by the visible and nonvisible light are partially coextensive.

The basic structure of the detection optics is also similar to that of FIG. 2, with the configuration shown with sublabels "1" being used to collect reflected light and the configuration shown with sublabels "2" being used to collect transmitted light. Each of these configurations includes a collimating lens 328, a focusing lens 332, and a polarizer 328, although other configurations using different optical elements are possible in alternative embodiments. The optical trains direct light to the light detectors 326, which may be embodied using any of the structures identified above, as well as with other structures.

The polarizers may comprise linear, circular, or elliptical polarizers in different embodiments and act to polarize the illumination light before it is incident on the object under study 304. The combination of illumination and detection polarizers may thus be used advantageously to make the optical measurements more sensitive to certain depths within the object under study 304. In a particular embodiment, the detection polarizers 328 are arranged with their optical axes substantially orthogonal to the optical axes of the illumination polarizers 310. In such a configuration, light received by the detectors 326 must undergo multiple scattering events to change the state of polarization sufficiently that it will not be blocked by the detection polarizers 326. Such states occur when the light penetrates the surface of the object under study 304 and is scattered back into the detection optics after many scattering events.

Figure 4:
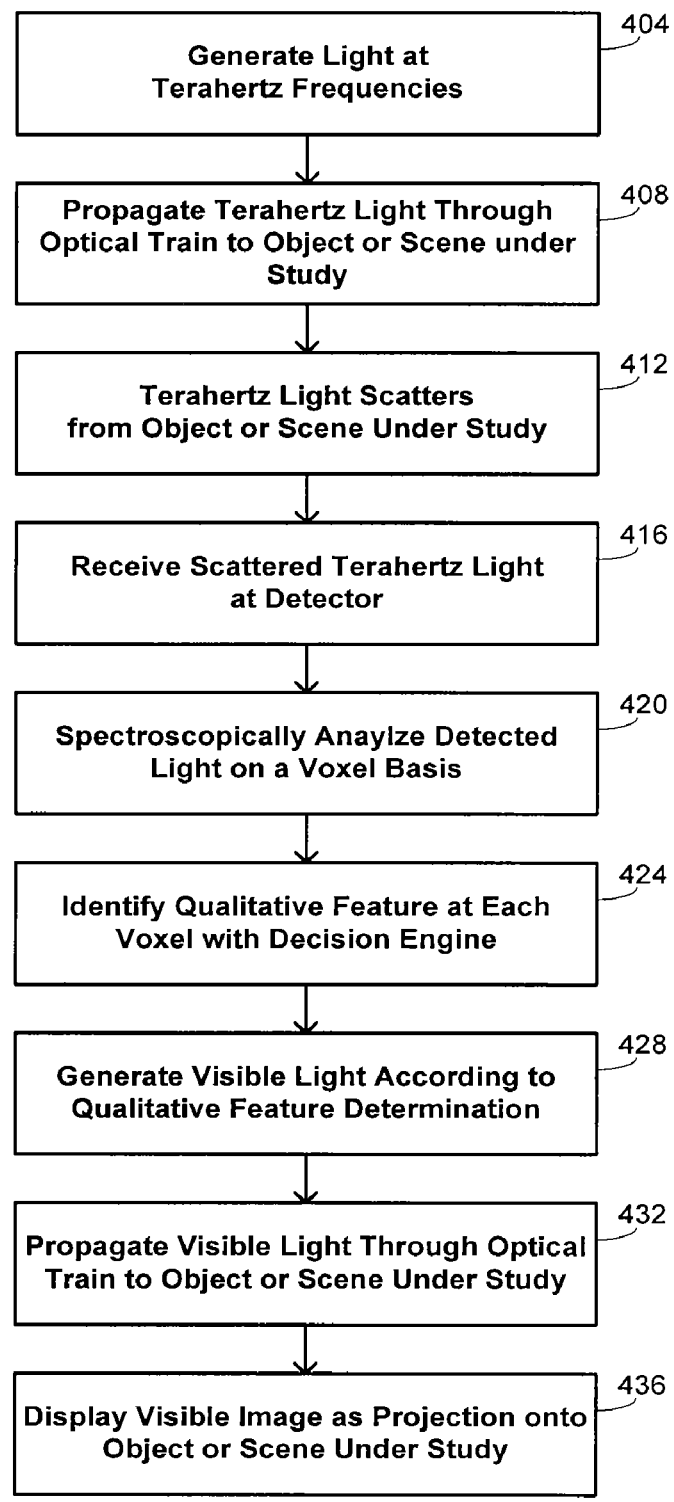
FIG. 4 is a flow diagram summarizing methods of the invention.

Methods of the invention are summarized with the flow diagram of FIG. 4, which sets forth a number of specific steps that may be performed in some embodiments of the invention. It should be appreciated, however, that the illustration of specific steps is not intended to exhaustive and limiting. In other embodiments of the invention, some of the steps may be omitted and/or some additional steps may be performed without departing from the intended scope of the invention. Furthermore, the illustration of the steps in a particular order in FIG. 4 is also not intended to be limiting. In some embodiments, the steps may be performed concurrently or in a different order than that shown in the drawing.

Methods of the invention begin by generating light at block 404 at nonvisible frequencies. In the particular embodiment shown in the drawing, the nonvisible frequencies comprise terahertz frequencies. This light is propagated at block 408 through an optical train to the object or scene under study, which scatters the light at block 412. The scattered light is received at a detector at block 416, permitting a spectroscopic analysis to be performed at block 420. The spectroscopic analysis is generally performed on a voxel-by-voxel basis using techniques known in the art for spectroscopic analysis. Basically, such analytical techniques identify the wavelength and intensity of spectral peaks and correlate such information with the known spectral properties of various materials. In many instances, the light received by the detector may be spectroscopically complex and such known techniques permit identification of potentially multiple characteristics at each voxel.

The identification of qualitative features of the object or scene under study on a voxel-by-voxel basis may thus be achieved through the use of a decision engine at block 424. There are a number of different ways in which a decision engine may be implemented, all of them providing a mechanism for mapping the spectroscopic information to qualitative-feature information. For example, the decision engine might be a purely passive engine that consistent maps a spectrum having particular features to a particular qualitative feature. Or, the decision engine might be an active engine that adapts correctively to information.

One such active engine makes use of a neural network, which typically includes a plurality of nodes, each of which has a weight value associated with it. The network includes an input layer having a plurality of input nodes Ix and an output layer having a plurality of output nodes Oy with at least one layer therebetween. The activity of the input nodes Ix represents the raw spectroscopic information that is fed into the network and the behavior of the output nodes Oy represents the interpretation drawn by the network in defining qualitative features. The intermediate layer(s) act as weight layers to assign relative weights to the different inputs or combinations of the inputs from the input nodes Ix. A variety of different forms of transform functions (sometimes called transfer functions) define how the weighting factors are applied, with common transform functions including linear ramp functions, Heaviside step functions, and sigmoid functions, among others.

In order to train the neural network, connections and weights are usually assigned randomly and output values are calculated for sample input values. The output values are compared against the correct interpretation as it would be made by a human with some known samples. If the output value is incorrect when compared against such a test interpretation, the neural network modifies itself to arrive at the correct output value. This is achieved by connecting or disconnecting certain nodes and/or adjusting the weight values of the nodes during the training through a plurality of iterations. Once the training is completed, the resulting layer/node configuration and corresponding weights represent a trained neural network. The trained neural network is then ready to receive unknown spectroscopic data and develop qualitative-feature identifications in an adaptive fashion. Classical neural networks include Kohonen nets, feed-forward nets, and back-propagation nets. These different neural nets have different methods of adjusting the weights and organizing the respective neural network during the training process.

The neural network continues to be adaptive as it interacts with users of the spectroscopic illuminator, with different uses of the illuminator acting as further training for the network. As errors are detected in the qualitative identifications made by the neural network, the node structure may be altered so that the correct identification results. In this way, feedback information acquired by the neural network is used in improving its qualitative identifications over time. As part of these processes, the spectral characteristics and/or qualitative characteristics may be recorded.

At block 428 of FIG. 4, visible light is generated according to the qualitative feature determinations. This may be done in a number of different ways, such as by providing light at particular frequency or intensity according to the qualitative feature identification, and/or by using some particular temporal dependence of frequency or intensity by having the light pulse or change its color in a specified way. The generated visible light is accordingly propagated through the optical train at block 432 to the object or scene under study and used at block 436 to display a visual image as a projection onto the object or scene under study. This propagation and display is performed in a manner that illuminates different voxels comprised by the object or scene in different ways according to the qualitative feature identifications.

There are certain differences that may arise between the use of pulsed and continuous wave operation. With pulsed illumination, for example, the integration may be gated. With continuous-wave illumination, the continuous-wave signal may instead be chopped, with detection performed synchronously. If the source power is limited, the average power $P_{avg}$ is $$P_{avg} = P_{peak} D,$$

where $P_{peak}$ is the peak power and D is the duty cycle. The average power $P_{avg}$ may be controlled to a desired level and for pulsed operation D☐1 to prevent overheating. For continuous operation, peak power $P_{peak}$ is thus the limiting factor, such as might result with diode reverse breakdown. This is contrasted with continuous-wave operation, in which D=1.

Figure 5:
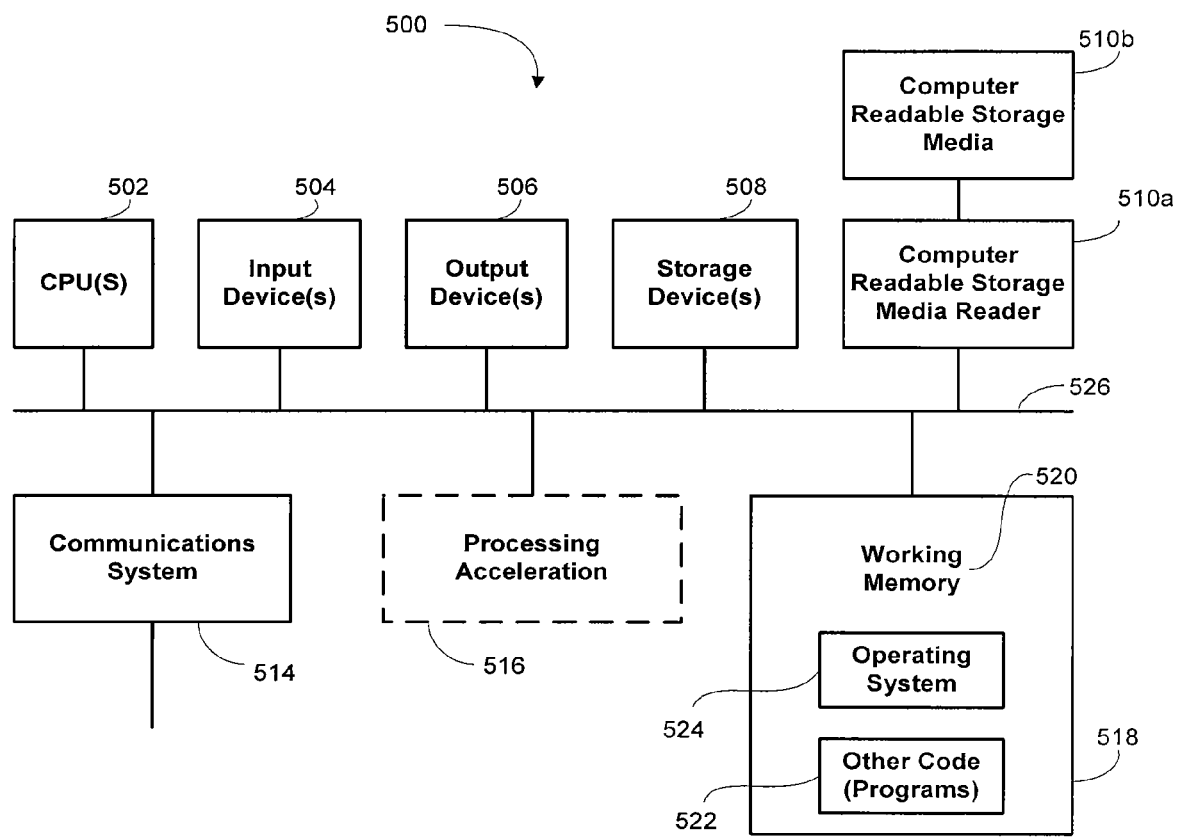
FIG. 5 is a schematic representation of a controller system that may be used to manage functionality of illuminators in accordance with embodiments of the invention.

Management of the functionality discussed herein for the controller 250 or 350 may be performed using a computational device identified generically by reference number 500 in FIG. 5. This drawing broadly illustrates how individual system elements may be implemented in a separated or more integrated manner. The computational device 500 is shown comprised of hardware elements that are electrically coupled via bus 526. The hardware elements include a processor 502, an input device 504, an output device 506, a storage device 508, a computer-readable storage media reader 510a, a communications system 514, a processing acceleration unit 516 such as a DSP or special-purpose processor, and a memory 518. The computer-readable storage media reader 510a is further connected to a computer-readable storage medium 510b, the combination comprehensively representing remote, local, fixed, and/or removable storage devices plus storage media for temporarily and/or more permanently containing computer-readable information. The communications system 514 may comprise a wired, wireless, modem, and/or other type of interfacing connection and permits data to be exchanged with external devices.

The computational device 500 also comprises software elements, shown as being currently located within working memory 520, including an operating system 524 and other code 522, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

EXAMPLES

While transspectral illumination has many potential applications, one particular use is found in the illumination of biological tissue, particular when applied during treatment of human beings or animals. For example, in surgical applications, tissue may be illuminated with the spectroscopic illuminator at terahertz frequencies, with malignant tissues having different characteristic spectral signatures than that of healthy tissue. In some instances, the spectral signatures may be correlated with the type and/or progress of cancerous development, providing information that is useful to a physician in diagnosis.

Once these signatures have been identified from the collected scattered light, the tissue areas when they originate may be illuminated by a visible light signal in a manner controlled to illuminate the area in a way that makes those characteristics apparent to an observer. This may be done using any of the techniques described earlier, such as by illuminating the area with light of a particular color, by illuminating the area with light of a particular intensity, and/or by illuminating the area with light that changes its intensity in a particular way, as well as by using other techniques. In particular, the visible light signal illuminates areas that contain cancerous cells, making the illuminator useful during processes of removing such cells surgically or by ablation during other procedures.

The illuminator may be used substantially continuously during such procedures, with the visible-light illumination being modified as the character of the tissue changes. This allows the area and depth of cutting during surgery to be identified and limited by the disappearance of the marking visible-light signal. For instance, if a particular type of cancerous cell is identified with terahertz radiation, those cells could be illuminated by a distinctive bright blue light that pulses at a suitable interval. When this light is no longer observed by the practitioner after a surgical cut, it will be apparent with a high degree of confidence that those cancerous cells have been successfully removed.

In another example, the illuminator is used to image an object or scene under study that is at least partially concealed by a concealing object or scene that is at least partly opaque at visible wavelengths. The nonvisible light is used to penetrate the concealing object in acquiring information about the object under study, with visible light then providing a direct image of the object under study without damage to the concealing object. For instance, in one application, wounds may be imaged in this way through bandages or through a cast.

In yet a further application, an embodiment of the invention may incorporate various forms of additional apparatus, one example of which is night-vision systems; such system include a variety of systems important in the detection of concealed explosives. A beam or beams of electromagnetic radiation in the terahertz range of about 0.1-10 THz may be projected from a projector upon a scene in any of several formats, including raster scan and other formats, or by directing it at a specific or selected areas within the scene. Such a projection with a corresponding receiver may be mounted on a vehicle, may be stationary, or may be portable in different embodiments.

It is known that various materials may have a distinctive spectral response or reflection in the terahertz region. For instance, concealed or buried explosives have been shown to have this response, even if covered by ordinary materials such as clothing. The reflected beams from the scene are collected by the receiver and subjected to spectral analysis. If any of the spectra obtained from the returned beams are of interest, a selected type of light beam may then be projected back at that spot of interest by another or the same projector. This selected beam of light may comprise light within the visible spectrum or may comprise a wavelength of infrared light that is invisible to the naked eye, but within the range of detection of night-vision equipment. This enables personnel having infrared or night-vision capabilities effectively to see the projected light, which may indicate explosive material or other material of interest or other selectable features from their diverse vantage points, as the scene is bathed in infrared light on the areas of interest. These areas appear visibly through their night-vision goggles or on other display devices.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method of generating a visible image of an object or scene under study, the method comprising:
    illuminating at least a portion of the object or scene under study with light outside a visible portion of an electromagnetic spectrum;
    receiving light scattered by the object or scene under study;
    spectroscopically analyzing the received light for a plurality of volume elements of the object or scene under study;
    identifying a respective qualitative feature of the object or scene under study at least one of the plurality of volume elements; and
    propagating visible light to the at least one of the plurality of volume elements according to the respective qualitative feature of the object or scene under study at the at least one of the plurality of volume elements, to display a visual image as a projection onto the object or scene under study, in order to illuminate different volume elements in different ways according to the presence or absence of the qualitative feature.

2. The method recited in claim 1 wherein the at least one of the plurality of volume elements is each of the plurality of volume elements.

3. The method recited in claim 1 wherein the light outside the visible portion of the electromagnetic spectrum comprises a frequency between 0.1 and 100 THz.

4. The method recited in claim 1 wherein the light outside the visible portion of the electromagnetic spectrum comprises a frequency between 0.1 and 30 THz.

5. The method recited in claim 1 wherein the light outside the visible portion of the electromagnetic spectrum comprises a frequency between 1 and 10 THz.

6. The method recited in claim 1 wherein the light scattered by the object or scene under study comprises light reflected by the object or scene under study.

7. The method recited in claim 1 wherein the light scattered by the object or scene under study comprises light transmitted through the object or scene under study.

8. The method recited in claim 1 wherein:
illuminating the at least a portion of the object or scene under study comprises polarizing the light outside the visible portion of the electromagnetic spectrum with a first polarization; and
receiving the light scattered by the object or scene under study comprises polarizing the light scattered by the object or scene under study with a second polarization; and
the first and second polarizations are in a substantially crossed configuration.

9. The method recited in claim 1 wherein:
illuminating the at least a portion of the object or scene under study comprises propagating the light outside the visible portion of the electromagnetic spectrum along an optical path to the object or scene under study; and
propagating the visible light to each of the plurality of volume elements comprises propagating the visible light along at least a portion of the optical path.

10. The method recited in claim 1 wherein illuminating the at least a portion of the object or scene under study comprises filtering the light to generate the light outside the visible portion of the electromagnetic spectrum.

11. The method recited in claim 1 wherein illuminating the at least a portion of the object or scene under study comprises illuminating the at least a portion of the object or scene under study with a substantially continuous beam of the light outside the visible portion of the electromagnetic spectrum.

12. The method recited in claim 1 wherein illuminating the at least a portion of the object or scene under study comprises illuminating the at least a portion of the object or scene under study with a pulsed beam of the light outside the visible portion of the electromagnetic spectrum.

13. The method recited in claim 1 wherein the object or scene under study comprises biological tissue.

14. The method recited in claim 1 wherein propagating visible light to the at least one of the plurality of volume elements comprises:
propagating a wavelength of light outside the human visible spectrum to the at least one of the plurality of volume elements; and
receiving a reflection from the at least one of the plurality of volume elements with equipment configured to provide a visible image at the wavelength of light.

15. A system for generating a visible image of an object or scene under study, the system comprising:
a light source;
a light detector; and
a controller in communication with the light source and the light detector, the controller having:
instructions to illuminate at least a portion of the object or scene under study with the light source using light outside a visible portion of an electromagnetic spectrum;
instructions to receive light scattered by the object or scene under study with the light detector;
instructions to spectroscopically analyze the received light for a plurality of volume elements of the object or scene under study;
instructions to identify a respective qualitative feature of the object or scene under study at least one of the plurality of volume elements; and
instructions to propagate visible light with the light source to the at least one of the plurality of volume elements according to the respective qualitative feature of the object or scene under study at the at least one of the plurality of volume elements, to display a visual image as a projection onto the object or scene under study, in order to illuminate different volume elements in different ways according to the presence or absence of the qualitative feature.

16. The system recited in claim 15 wherein the at least one of the plurality of volume elements is each of the plurality of volume elements.

17. The system recited in claim 15 wherein the light outside the visible portion of the electromagnetic spectrum comprises a frequency between 0.1 and 100 THz.

18. The system recited in claim 15 wherein the light outside the visible portion of the electromagnetic spectrum comprises a frequency between 0.1 and 30 THz.

19. The system recited in claim 15 wherein the light outside the visible portion of the electromagnetic spectrum comprises a frequency between 1 and 10 THz.

20. The system recited in claim 15 wherein the light scattered by the object or scene under study comprises light reflected by the object or scene under study.

21. The system recited in claim 15 wherein the light scattered by the object or scene under study comprises light transmitted through the object or scene under study.

22. The system recited in claim 15 further comprising:
a first polarizer disposed between the light source and the object or scene under study; and
a second polarizer disposed between the object or scene under study and the light detector,
wherein:
the first and second polarizer are in a substantially crossed configuration;
the instructions to illuminate the at least a portion of the object or scene under study comprise instructions to polarize the light outside the visible portion of the electromagnetic spectrum with the first polarizer; and
the instructions for receiving the light scattered by the object or scene under study comprise instructions to polarize the light scattered by the object or scene under study with the second polarizer.

23. The system recited in claim 15 wherein:
the instructions to illuminate the at least a portion of the object or scene under study comprise instructions to propagate the light outside the visible portion of the electromagnetic spectrum along an optical path to the object or scene under study; and the instructions to propagate the visible light to each of the plurality of volume elements comprise instructions to propagate the visible light along at least a portion of the optical path.

24. The system recited in claim 15 further comprising a filter disposed between the light source and the object or scene under study to generate the light outside the visible portion of the electromagnetic spectrum.

25. The system recited in claim 15 wherein the light source is configured to illuminate the object or scene under study with a substantially continuous beam of the light outside the visible portion of the electromagnetic spectrum.

26. The system recited in claim 15 wherein the light source is configured to illuminate the object or scene under study with a pulsed beam of the light outside the visible portion of the electromagnetic spectrum.

27. The system recited in claim 15 wherein the object or scene under study comprises biological tissue.

28. The system recited in claim 15 further comprising equipment configured to provide a visible image at a wavelength of light outside the human visible spectrum, wherein the instructions to propagate visible light to the at least one of the plurality of volume elements comprises:
  instructions to propagate the wavelength of light to the at least one of the plurality of volume elements; and
  instructions to receive a reflection from the at least one of the plurality of volume elements with the equipment.

* * * * *